United States Patent [19]

Soma et al.

[11] 4,237,294
[45] Dec. 2, 1980

[54] 2,2,6,6-TETRAMETHYLPIPERIDINE DERIVATIVES

[75] Inventors: Nobuo Soma, Tokyo; Syoji Morimura, Kanagawa; Takao Yoshioka, Tokyo; Tomoyuki Kurumada, Tokyo, all of Japan

[73] Assignees: Sankyo Company, Limited, Tokyo, Japan; Ciba-Geigy Corporation, New York, N.Y.

[21] Appl. No.: 49,816

[22] Filed: Jun. 18, 1979

[30] Foreign Application Priority Data

Jul. 3, 1978 [JP] Japan .................. 53-80639

[51] Int. Cl.$^3$ ............ C07D 401/04; C07D 405/104
[52] U.S. Cl. ........................ 546/20; 546/19; 260/45.8 NT; 260/45.8 NZ
[58] Field of Search ............... 546/19, 20

[56] References Cited

U.S. PATENT DOCUMENTS

| | | | |
|---|---|---|---|
| 3,899,464 | 8/1975 | Murayama et al. | 546/19 |
| 3,992,390 | 11/1976 | Holt et al. | 546/16 |
| 4,021,432 | 5/1977 | Holt et al. | 546/16 |
| 4,097,587 | 6/1978 | Soma et al. | 546/20 |
| 4,125,533 | 11/1978 | Murayama et al. | 546/19 |
| 4,141,883 | 2/1979 | Soma et al. | 546/16 |

OTHER PUBLICATIONS

Chemical Abstracts, vol. 83, ITEM 60490h (1975), Abstracting German Offenlegungsschrift, 2,349,962, Apr. 18, 1974.

Primary Examiner—Henry R. Jiles
Assistant Examiner—Robert T. Bond
Attorney, Agent, or Firm—Luther A. R. Hall

[57] ABSTRACT 2,2,6,6-Tetramethylpiperidine derivatives having the formula

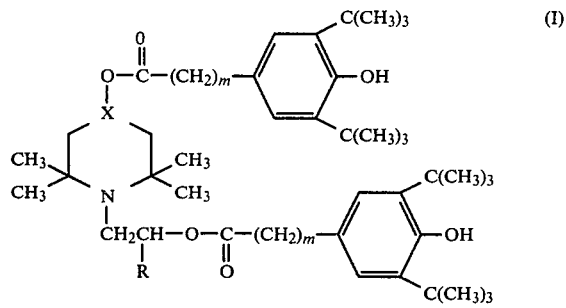

(I)

wherein:
X represents a group of formula

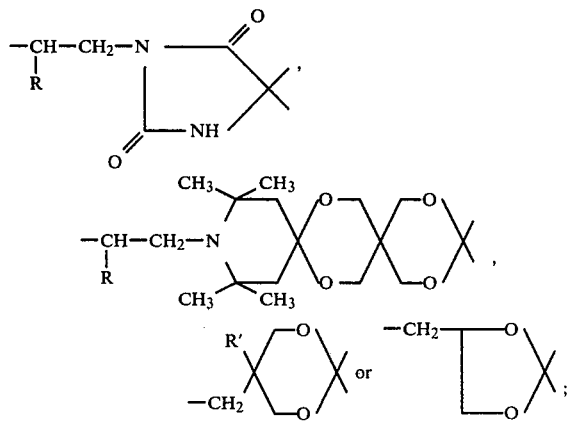

R represents a hydrogen atom, methyl group, ethyl group, phenoxymethyl group or phenyl group;
R' represents a methyl group or ethyl group; and
m represents 0, 1 or 2, are excellent stabilizers for synthetic polymers.

3 Claims, No Drawings

2,2,6,6-TETRAMETHYLPIPERIDINE DERIVATIVES

The invention relates to novel 2,2,6,6-tetramethylpiperidine derivatives and synthetic polymer compositions stabilized by adding therein said derivatives.

Heretofore, there are disclosed in Japanese Patent Application No. 48-65182, as laid open to public inspection, 2,2,6,6-tetramethylpiperidine derivatives containing 3,5-di-tert-butyl-4-hydroxyphenyl group in the molecule and having the formula

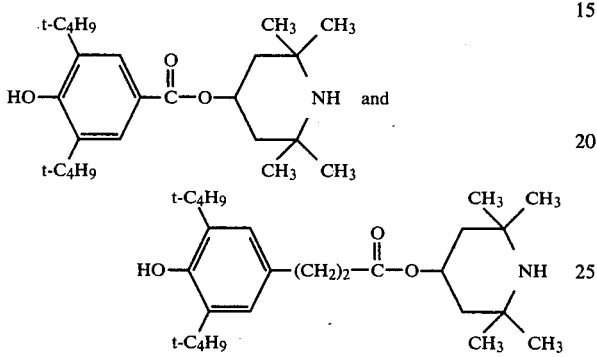

as stabilizers for synthetic polymers. Further, there are disclosed in Japanese Patent Application No. 48-65180, as laid open to public inspection, the N-methyl derivatives of the above-mentioned compounds. Furthermore, there are illustrated in Japanese Patent Application No. 49-64635, as laid open to public inspection compounds

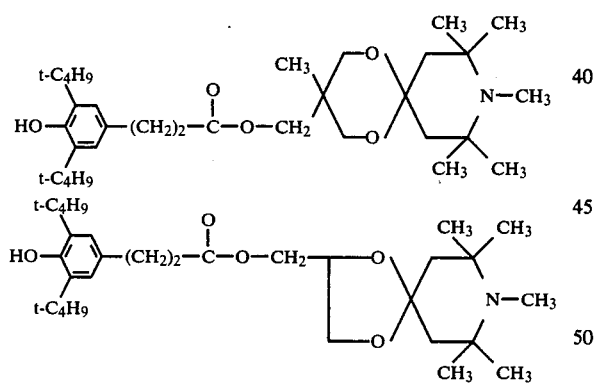

as light stabilizers.

The inventors have found that 2,2,6,6-tetramethylpiperidine derivatives in which the above-mentioned known compounds are linked with a group comprising 3,5-di-t-butyl-4-hydroxyphenyl at 1-position of the piperidine nucleus show a light stabilizing activity, and at the same time, a superior heat-stabilizing activity for synthetic polymers and a processing stability upon heating. The compounds of the invention are hardly volatile and superior also with regard to the compatibility with polymers and the extraction-resistance therefrom.

The novel 2,2,6,6-tetramethylpiperidine derivatives of the invention are represented by the following formula (I):

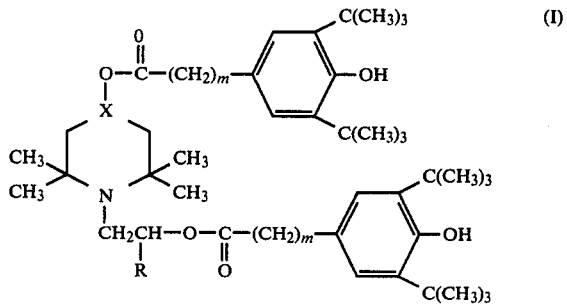

wherein:
X represents a group of formula

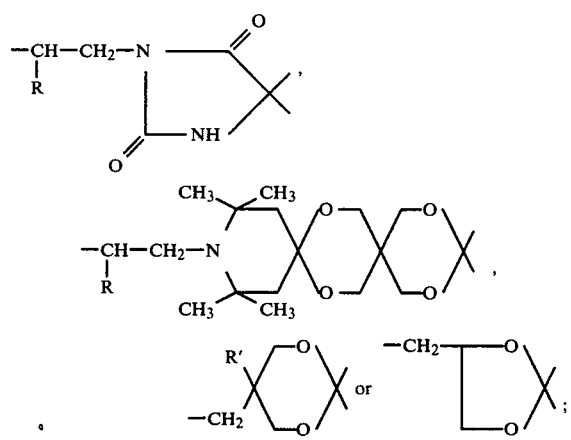

R represents a hydrogen atom, methyl group, ethyl group, phenoxymethyl group or phenyl group;
R' represents a methyl group or ethyl group; and
m represents 0, 1 or 2.

In formula (I), X is preferably a group of formula

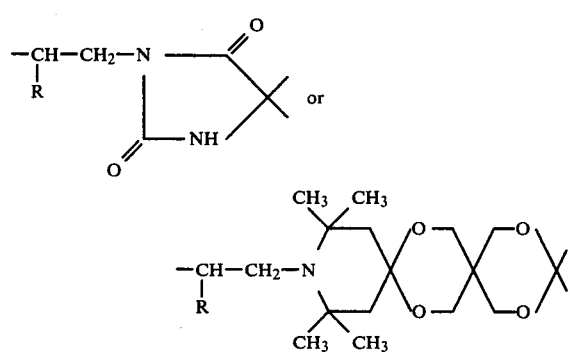

(R has the meanings defined above.).
R is preferably a hydrogen atom;
m is preferably 2; and
R' is preferably an ethyl group.

The following is a non-limiting list of the individual 2,2,6,6-tetramethylpiperidines of formula (I). The numbers appended in the list will be used in the following examples to identify the compounds.

(1)
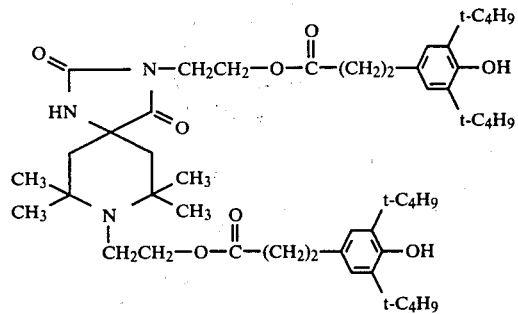
(2)
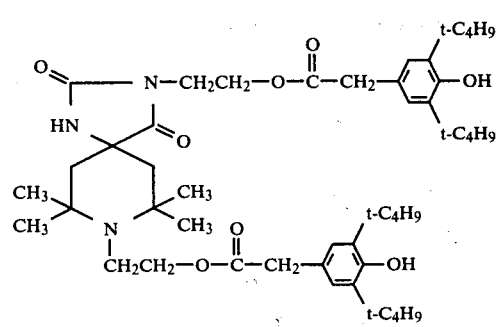
(3)
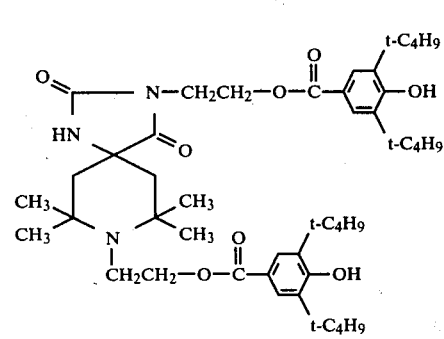
(4)
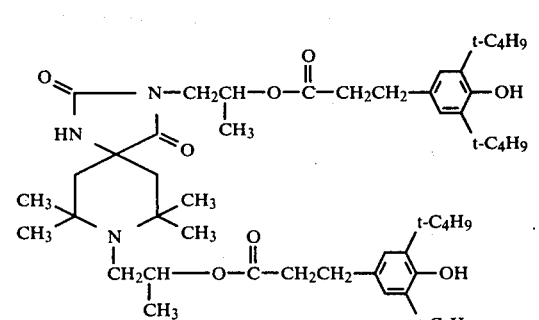
(5)
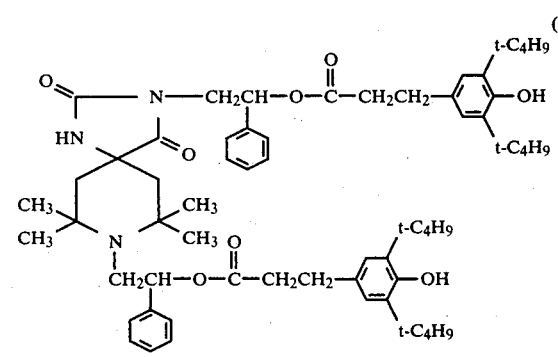
-continued
(6)
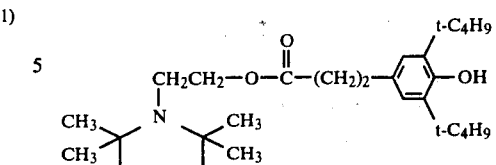
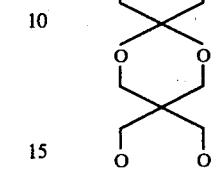
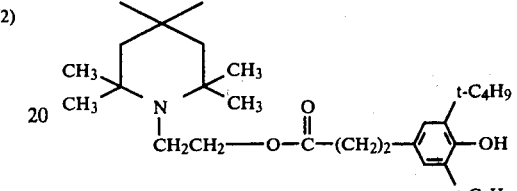
(7)
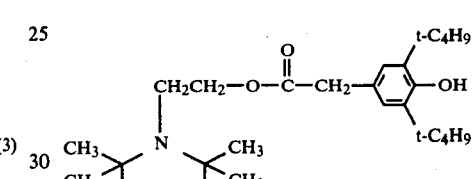
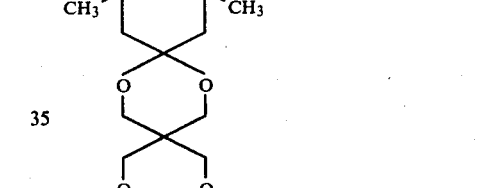
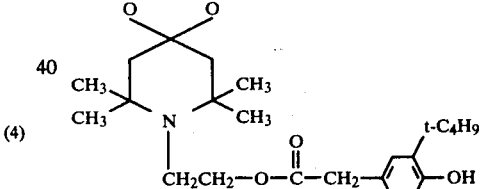
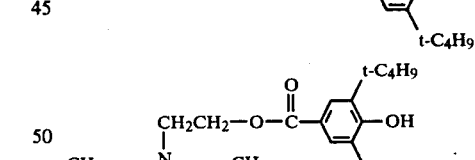
(8)
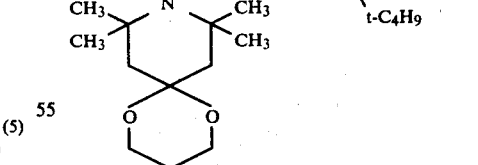
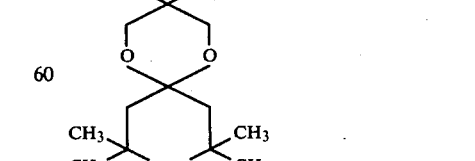
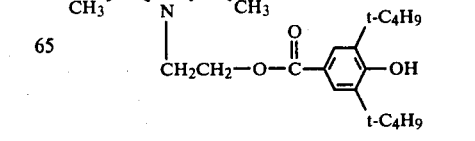

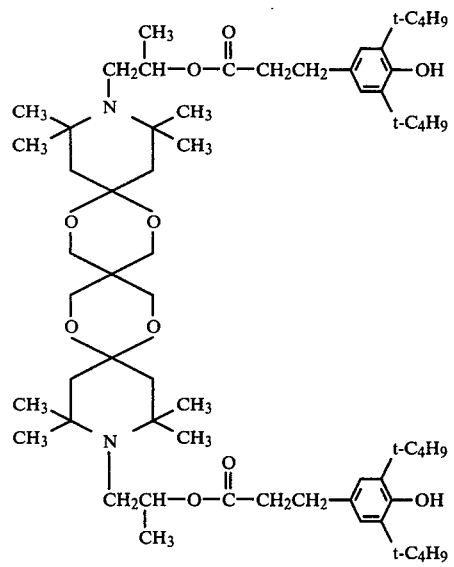
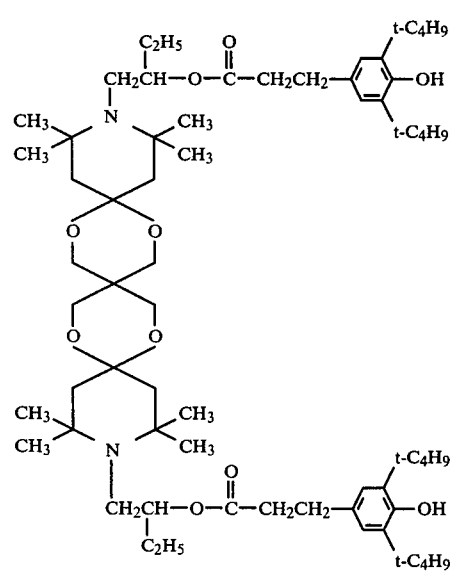
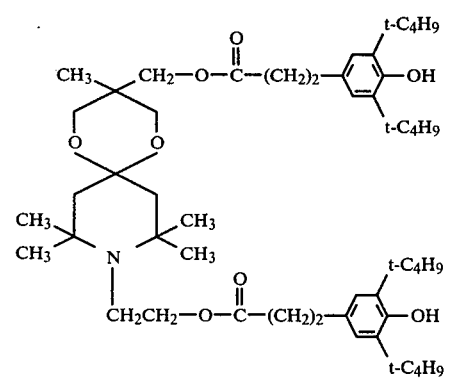
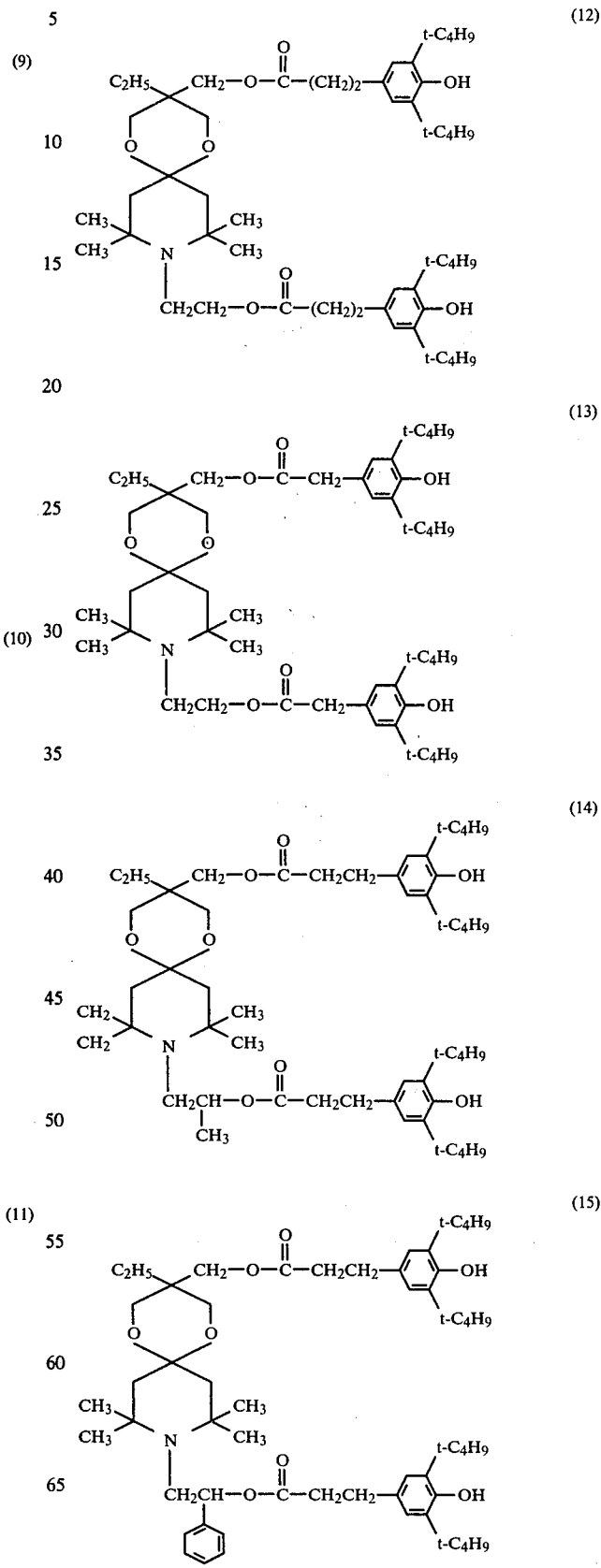

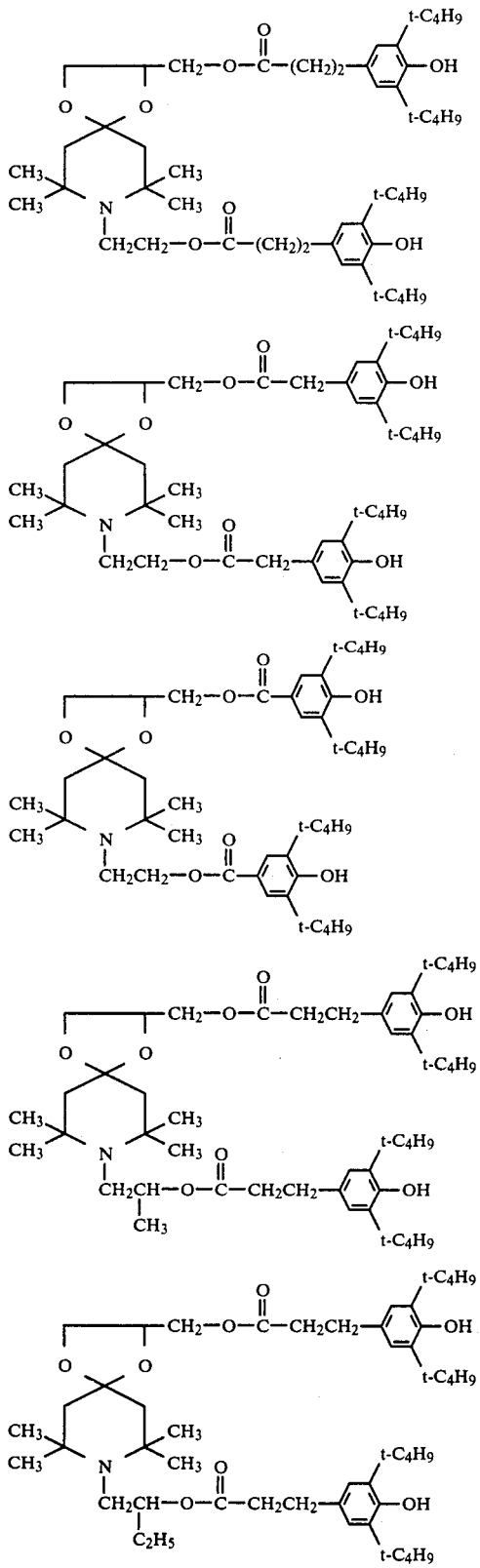

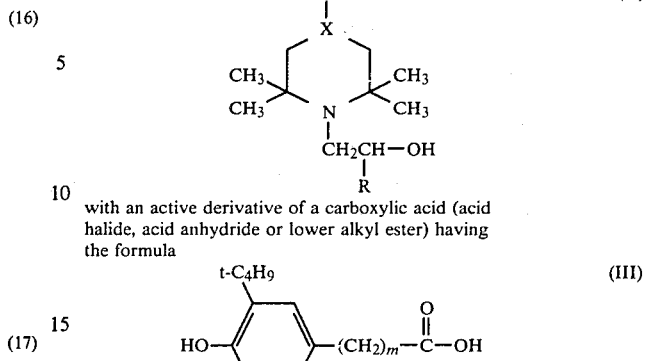

The 2,2,6,6-tetramethylpiperidine derivatives of formula (I) according to the invention may be prepared by reacting a compound of formula

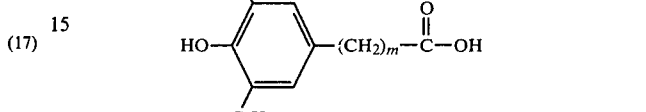

with an active derivative of a carboxylic acid (acid halide, acid anhydride or lower alkyl ester) having the formula $$\text{t-C}_4\text{H}_9 \qquad \text{(III)}$$

HO—⟨benzene⟩—(CH$_2$)$_m$—C(=O)—OH t-C$_4$H$_9$ (In the above formulae, X, R and m have the meanings defined above.)

When the reactive derivative employed is an ester of the acid, the reaction is preferably carried out in the presence of a strong base and of an inert organic solvent.

Examples of suitable solvents are aromatic and aliphatic hydrocarbons such as benzene, toluene, xylene, n-heptane, n-octane and isooctane. Suitable strong bases include, for example:strongly basic alkali metal compounds, such as sodium methoxide, sodium ethoxide, potassium hydroxide or lithium amide; or titanic acid compounds, such as tetraisopropyl titanate or tetrabutyl titanate. It is preferred that the reaction should be carried out with heating, preferably at a temperature from 80°–180° C.

When an acid halide is employed, the reaction is preferably carried out in the presence of an acid-binding agent and of an inert organic solvent. Examples of suitable solvents are: aromatic hydrocarbons, such as benzene, toluene and xylene; halogenated aliphatic hydrocarbons, such as chloroform and trichloroethane; and ethers, such as diethyl ether, tetrahydrofuran and dioxane. Suitable acid-binding agents include: alkali metal hydroxide, such as sodium hydroxide and potassium hydroxide; alkali metal carbonates, such as sodium carbonate and potassium carbonate; and organic bases, such as triethylamine and pyridine. The reaction is usually carried out at a temperature from 0°–130° C.

Where the reactive derivative is an acid anhydride, the reaction is preferably carried out in the presence of an inert organic solvent or in the absence of a solvent but using an excess of acid anhydride. Where a solvent is employed, it is selected from:aromatic hydrocarbons such as benzene, toluene and xylene; and ethers, such as dioxane, tetrahydrofuran and diethylene glycol dimethyl ether. The reaction temperature may preferably be any temperature from ambient to 160° C.

The 2,2,6,6-tetramethylpiperidine derivatives of formula (I) according to the invention can stabilize effectively wide varieties of synthetic polymers.

Synthetic polymers stabilized in this way include: olefin and diene polymers
including homopolymers of olefins and dienes (e.g. low-density, high-density and cross-linked polyethylenes, polypropylene, polyisobutylene, polymethylbutene-1, polymethylpentene-1, polyisoprene and polybutadiene), mixtures of such homopolymers (e.g.

mixtures of polypropylene and polyethylene, polypropylene and polybutene-1, or polypropylene and polyisobutylene), and copolymers of olefins and dienes (e.g. ethylene/propylene copolymers, propylene/butene-1 copolymers, propylene/isobutylene copolymers, ethylene/butene-1 copolymers, and terpolymers of ethylene and propylene with dienes such as hexadiene, dicyclopentadiene or ethylidene norbornene):

styrene polymers
including polystyrene, copolymers of styrene and of α-methylstyrene (e.g. styrene/butadiene copolymers, styrene/acrylonitrile copolymers, styrene/acrylonitrile/methylmethacrylate copolymers, styrene/acrylonitrile/acrylic ester copolymers, styrene/acrylonitrile copolymers modified wih acrylic ester polymers to provide impact strength, and styrene polymers modified with ethylene/propylene/diene elastomers to provide impact strength), and graft copolymers of styrene (e.g. polymers in which styrene is grafted onto polybutadiene, and polymers in which styrene and acrylonitrile are grafted onto polybutadiene as well as mixtures thereof with the aforementioned styrene copolymers commonly known as acrylonitrile/butadiene/styrene or ABS plastics);

halogenated vinyl and vinylidene polymers
including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, and vinylidene chloride/vinyl acetate copolymers;

polymers derived from α,β-unsaturated acids
and derivatives thereof, including polyacrylates and polymethacrylates, polyacrylic amides and polyacrylonitrile;

polymers derived from unsaturated alcohols and amines and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate, and polyallyl melamine, and copolymers thereof with other ethylenically unsaturated monomers (e.g. ethylene/vinyl acetate copolymers);

epoxy polymers
including homopolymers and copolymers derived from epoxides (e.g. polyethylene oxide), and polymers derived from bis-glycidyl ethers;

polyacetals, polyalkylene oxides and polyphenylene oxides
including polyoxymethylene, oxymethylene/ethylene oxide copolymers, polyoxyethylene, polypropylene oxide, polyisobutylene oxide and polyphenylene oxides;

polyurethanes and polyureas;
polycarbonates;
polysulphones;
polyamides and copolyamides
derivated from diamines and dicarboxylic acids and/or from aminocarboxylic acids or the corresponding lactams, including nylon-6, nylon-6,6, nylon-6,10, nylon-11 and nylon-12;

polyesters
derived from dicarboxylic acids and dialcohols and/or from hydroxycarboxylic acids and the corresponding lactones, e.g. polyethylene glycol terephthalate and poly-1,4-dimethylol-cyclohexane terephthalate:

cross-linked polymers
derived from aldehydes together with phenols, ureas or melamines, e.g. phenol/formaldehyde, urea/formaldehyde and melamine/formaldehyde resins;

alkyd resins
e.g. glycerol/phthalic acid resins and mixtures thereof with melamine/formaldehyde resins;

unsaturated polyester resins
derived from copolyesters of saturated and unsaturated dicarboxylic acids with polyhydric alcohols as well as from vinyl compounds as cross-linking agents, and also halogenated flame-resistant modifications thereof.

The amount of the stabilizers of the invention needed for effective stabilization of organic polymers will depend on a variety of factors, such as the type and properties of the polymer concerned, its intended use, and the presence of other stabilizers. It is generally satisfactory to use from 0.01% to 5% by weight of the stabilizers of the invention, based on the weight of the polymer, but the most effective range will vary with the type of polymer; viz. 0.01% to 2.0%, preferably 0.02% to 1.0%, by weight for olefin, diene and styrene polymers; 0.01% to 1.0%, preferably 0.02% to 0.5%, by weight for vinyl and vinylidene polymers; and 0.01% to 5.0%, preferably 0.02% to 2.0%, by weight for polyurethanes and polyamides. If desired, two or more of the stabilizers of the invention may be used together.

The stabilizers of the invention may readily be incorporated into organic polymers by conventional techniques at any convenient stage prior to the manufacture of shaped articles therefrom. For example, the stabilizer may be mixed with the polymer in dry powder form, or a suspension or emulsion of the stabilizer may be mixed with a solution, suspension or emulsion of the polymer.

The stabilized polymeric composition of the invention may optionally also contain one or more of various additives conventionally used in polymer technology such as the additives listed in British Patent Specification No. 1,401,924, at pages 11 to 13.

The invention is further illustrated by the following Examples, in which all parts are by weight:

EXAMPLE 1

3,8-Bis[2-{3-(3,5-di-tert-butyl-4-hydroxyphenyl)propionyloxy}ethyl]-7,7,9,9-tetramethyl-2,4-dioxo-1,3,8-triazaspiro[4.5]decane (Compound No. 1)

A mixture of 2.9 g of 3,8-bis(2-hydroxyethyl)-7,7,9,9-tetramethyl-2,4-dioxo-1,3,8-triazaspiro [4.5]decane, 6.4 g of methyl 3-(3,5-di-tert-butyl-4-hydroxyphenyl)propionate and 0.3 g of sodium methoxide was refluxed for 8 hours in 300 ml of xylene, while removing 250 ml of xylene together with methanol formed in situ. After completion of the reaction, xylene was evaporated from the reaction under reduced pressure and the resulting residue was recrystallized from ligroin, giving the desired compound in the form of white crystals melting at 178°–179° C.

EXAMPLE 2

2-[3-(3,5-di-tert-butyl-4-hydroxyphenyl)propionyloxymethyl]-8-[2-{3-(3,5-di-tert-butyl-4-hydroxyphenyl)propionyloxy}ethyl]-7,7,9,9-tetramethyl-1,4-dioxa-8-azaspiro[4.5]decane (Compound No. 16)

A mixture of 5.5 g of 2-hydroxymethyl-8-(2-hydroxyethyl)-7,7,9,9-tetramethyl-1,4-dioxa-8-azaspiro[4.5]-decane, 14 g of methyl 3-(3,5-di-tert-butyl-4-hydroxylphenyl)propionate and 0.25 g of lithium amide was heated for 2 hours in 200 ml of toluene, under argon stream. During the reaction, 120 ml of toluene was removed together with methanol formed in situ. After completion of the reaction, the reaction mixture was poured into water and extracted with benzene. The extract was dried over anhydrous potassium carbonate and the solvent was distilled out from the extract. The residue was purified by column chromatography through silica gel eluted first with benzene, then with a 10:5:4 by volume mixture of n-hexane, benzene and ethyl acetate, giving the desired compound in the form of a vitreous substance softening at 49°–53° C. The compound had an $R_f$ value of 0.37 on thin-layer chromatography on silica gel using a 7:2:1 by volume mixture of n-hexane, benzene and ethyl acetate as developing solvent.

EXAMPLE 3

3-[3-(3,5-Di-tert-butyl-4-hydroxyphenyl)propionyloxymethyl]-3-ethyl-9-[2-{3-(3,5-di-tert-butyl-4-hydroxyphenyl)-propionyloxy}ethyl]-8,8,10,10-tetramethyl-1,5-dioxa-9-azaspiro[5.5]undecane (Compound No. 12)

A mixture of 6.3 g of 3-hydroxymethyl-3-ethyl-9-(2-hydroxyethyl)-8,8,10,10-tetramethyl-1,5-dioxa-9-azaspiro[5.5]undecane, 14 g of methyl 3-(3,5-di-tertbutyl-4-hydroxyphenyl)propionate and 0.25 g of lithium amide was refluxed for 2 hours in 150 ml of toluene under argon stream. During the reaction, 120 ml of toluene was removed together with methanol formed in situ.

After completion of the reaction, the reaction mixture was treated in the similar manner as in Example 3, giving the desired compound in the form of a white powder softening at 51°–56° C. The compound had $R_f$ value of 0.41 on thin-layer chromatography on silica gel using a 7:2:1 by volume mixture of n-hexane, benzene and ethyl acetate as developing solvent.

EXAMPLE 4

2,2,4,4,14,14,16,16-Octamethyl-3,15-bis[2-{3-(3,5-ditert-butyl-4-hydroxyphenyl)propionyloxy}ethyl]-7,11,18,21-tetraoxa-3,15-diazatrispiro[5.2.2.5.2.2-]heneicosane (Compound No. 6)

A mixture of 20 g of 2,2,4,4,14,14,16,16-octamethyl-3,15-bis(2-hydroxyethyl)-7,11,18,21-tetraoxa-3,15-diazatrispiro[5.2.2.5.2.2]heneicosane, 26 g of methyl 3-(3,5-di-tert-butyl-4-hydroxyphenyl)propionate and 2 g of lithium amide was refluxed for 8 hours in 400 ml of toluene under argon stream. Following the procedures in Example 1, the residue was purified first by column chromatography through silica gel with a 9:1 by volume mixture of benzene and ethyl acetate, then by recrystallization from a 4:1 by volume mixture of n-hexane and benzene, giving the desired compound in the form of pale yellow crystals melting at 176°–178° C.

EXAMPLE 5

Testing of heat-stability

Mixture of 100 parts of unstabilized polypropylene powder (MFI=15) and 0.25 part of each in turn of the stabilizing compounds of the invention listed in Table 1 were blended and homogenized using a Brabender Plastograph at 200° C. for 10 minutes. The resulting masses were passed in a laboratory press to form sheets of thickness 2–3 mm. The sheets were heated and pressed using a compression-molding machine at 260° C. for 6 minutes and placed immediately into cold water to form sheets of thickness 0.5 mm. The sheets were cut to form test specimens of size 1×10 cm. Each test specimen was placed in a hot air-circulating thermostat at 150° C. and examined periodically at every 20 hours by bending test to determine the time to embrittlement. Similarly, control test specimens containing a known stabilizer, viz. (A) 4-[3-(3,5-di-tert-butyl)-4-hydroxyphenyl)propionyloxy]-2,2,6,6-tetramethylpiperidine, or (B) 4-[3-(3,5-di-tert-butyl-4-hydroxyphenyl)propionyloxy]-1,2,2,6,6-pentamethylpiperidine were prepared and tested for comparison. The results obtained are shown in Table 1.

TABLE 1

| Stabilizer Compound No. | Time to embrittlement |
|---|---|
| 1 | 320 hours |
| 6 | 220 |
| 12 | 520 |
| 16 | 560 |
| A | 80 |
| B | 100 |

EXAMPLE 6

Testing of light-stability

The sheets of thickness 0.5 mm obtained in Example 5 were subjected to a pressure of 12 tons by means of a hydraulic press at 260° C. for 6 minutes and then placed immediately into cold water to form films of thickness 0.1 mm. The films were cut to form test specimens of size 50×120 mm. Each test specimen was exposed to light in a Sunshine Weather Meter at a black panel temperature of 63°±3° C. and examined periodically to determine the percent elongation at break. The test results were expressed as a ratio of the time required for the test specimen to reach 50% elongation at break when a stabilizer was employed to the time when no stabilizer was employed. The results obtained are shown in Table 2.

TABLE 2

| Stabilizer Compound No. | Ratio |
|---|---|
| 1 | 4.4 |
| 6 | 3.8 |
| 12 | 3.7 |
| 16 | 4.5 |

EXAMPLE 7

Testing of heat-stability upon processing

Mixtures were made from 38 g of unstabilized polypropylene powder and 38 mg of each in turn of stabilizer compounds listed in Table 3 (0.1% by weight based on the polymer), blended and homogenized using a Brabender Plastograph at 200° C. for 10 minutes at 30 rpm/min. During the mixtures were hot, they were rolled to form plates of thickness 1–2 mm, which were cut finely to form test specimens. The melt flow index (MFI) of the test specimens were determined under the operation condition L and operation procedures B (automatic timing determination) as prescribed for in ASTMD-1238-73. Control test specimens containing no stabilizer or stabilizer (A) or (B) employed in Example 5 were prepared and tested for comparison. The results obtained are shown in Table 3.

TABLE 3

| Stabilizer compound No. | MFI |
|---|---|
| 1 | 5.5 |

TABLE 3-continued

| Stabilizer compound No. | MFI |
| --- | --- |
| 6 | 8.2 |
| 12 | 6.4 |
| 16 | 7.9 |
| A | 12.9 |
| B | 29.9 |
| none | 164 |

EXAMPLE 8

Testing of stabilizer evaporation 6 to 8 mg of each in turn of stabilizer compounds listed in Table 4 was placed on a thermobalance and heated under conditions of 50 ml/min. of air flow and 5° C./min. of temperature elevation. The percentage of remained stabilizer was measured at 250° C. and 300° C. The results are obtained are shown in Table 4.

TABLE 4

| Stabilizer compound No. | Remaining amount (%) 250° C. | 300° C. |
| --- | --- | --- |
| 1 | 98.3 | 92.7 |
| 12 | 99.0 | 96.2 |
| 16 | 100.0 | 98.7 |

What is claimed is:

1. A 2,2,6,6-tetramethylpiperidine compound having the formula

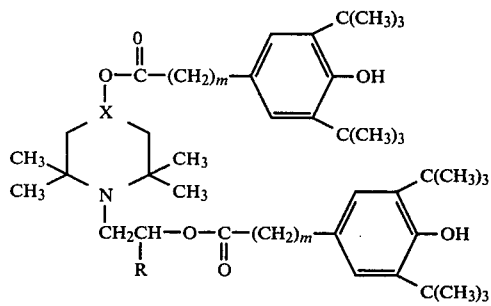

wherein:

X represents a group of formula

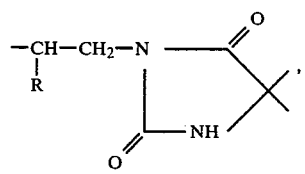

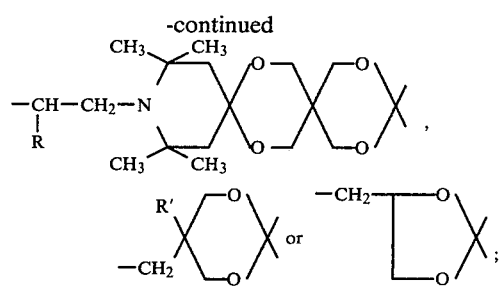

R represents a hydrogen atom;
represents an ethyl group; and
m represents 2.

2. A compound as claimed in claim 1 having the formula

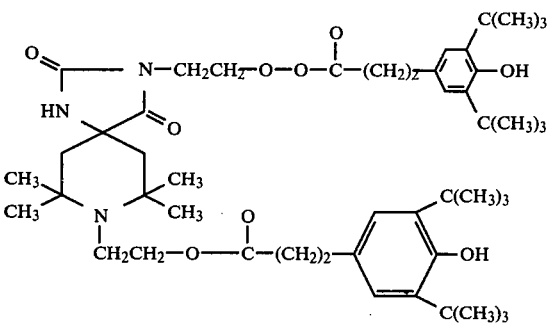

3. A compound as claimed in claim 1 having the formula

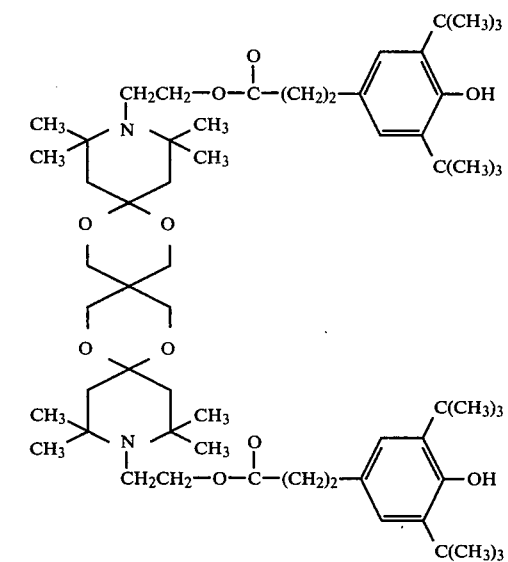

* * * * *

UNITED STATES PATENT AND TRADEMARK OFFICE
CERTIFICATE OF CORRECTION

PATENT NO. : 4,237,294
DATED : December 2, 1980
INVENTOR(S) : Nobuo Soma, Syoji Morimura, Takao Yoshioka, Tomoyuki Kurumada It is certified that error appears in the above–identified patent and that said Letters Patent are hereby corrected as shown below:

Claim 1, Column 14, Line 14 reads:

"represents an ethyl group; and"

Should read:

"R' represents an ethyl group; and"

Claim 2, Column 14, Line 20 reads:

$$\text{"}\ldots N\text{-}CH_2CH_2\text{-}O\text{-}O\text{-}\overset{\overset{O}{\|}}{C}\text{-}(CH_2)_2\text{-}\ldots\text{"}$$

Should read:

$$\text{"}\ldots N\text{-}CH_2CH_2\text{-}O\text{-}\overset{\overset{O}{\|}}{C}\text{-}(CH_2)_2\text{-}\ldots\text{"}$$

UNITED STATES PATENT AND TRADEMARK OFFICE
CERTIFICATE OF CORRECTION

PATENT NO. : 4,237,294
DATED : December 2, 1980
INVENTOR(S) : Nobuo Soma, Syoji Morimura, Takao Yoshioka, Tomoyuki Kurumada It is certified that error appears in the above-identified patent and that said Letters Patent are hereby corrected as shown below:

<u>Claim 2</u>, Column 14, Line 28 reads:

"$CH_2CH_2-O-\overset{O}{\underset{|}{C}}-(CH_2)_2-\ldots$"

Should read:

"$CH_2CH_2-O-\overset{O}{\underset{\|}{C}}-(CH_2)_2-\ldots$"

<u>Claim 3</u>, Column 14, Line 37 reads:

"$CH_2CH_2-O-\overset{O}{\underset{|}{C}}-(CH_2)_2-\ldots$"

Should read:

"$CH_2CH_2-O-\overset{O}{\underset{\|}{C}}-(CH_2)_2-\ldots$"

UNITED STATES PATENT AND TRADEMARK OFFICE
CERTIFICATE OF CORRECTION

PATENT NO. : 4,237,294  
DATED : December 2, 1980  
INVENTOR(S) : Nobuo Soma, Syoji Morimura, Takao Yoshioka, Tomoyuki Kurumada It is certified that error appears in the above-identified patent and that said Letters Patent are hereby corrected as shown below:

Claim 3, Column 14, Line 54 reads:

should read:

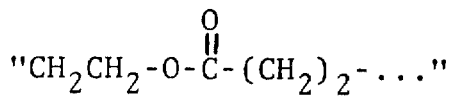

Signed and Sealed this

Twenty-first Day of April 1981

[SEAL]

Attest:

Attesting Officer

RENE D. TEGTMEYER

Acting Commissioner of Patents and Trademarks